(12) United States Patent
Kethman et al.

(10) Patent No.: US 9,801,638 B2
(45) Date of Patent: Oct. 31, 2017

(54) MULTI-COMPONENT DETACHABLE JAW TOOLS AND METHODS OF USING AND MAKING SAME

(75) Inventors: William Kethman, Houston, TX (US);
Dann Schwartz, Metairie, LA (US);
Steve Allen Franseen, Broomfield, CO (US)

(73) Assignee: The Administrator of the Tulane Educational Fund, New Orleans, LA (US)

( * ) Notice: Subject to any disclaimer, the term of this patent is extended or adjusted under 35 U.S.C. 154(b) by 838 days.

(21) Appl. No.: 14/006,661

(22) PCT Filed: Mar. 21, 2012

(86) PCT No.: PCT/US2012/029965
§ 371 (c)(1),
(2), (4) Date: Mar. 28, 2014

(87) PCT Pub. No.: WO2012/129317
PCT Pub. Date: Sep. 27, 2012

(65) Prior Publication Data
US 2014/0236170 A1    Aug. 21, 2014

Related U.S. Application Data

(60) Provisional application No. 61/465,564, filed on Mar. 21, 2011.

(51) Int. Cl.
*A61B 17/122* (2006.01)
*A61B 17/00* (2006.01)

(52) U.S. Cl.
CPC ........ *A61B 17/122* (2013.01); *A61B 17/1227* (2013.01); *A61B 2017/00477* (2013.01);
(Continued)

(58) Field of Classification Search
CPC ............. A61B 17/122; A61B 17/1222; A61B 2017/1225; A61B 17/1227; A61B 17/128;
(Continued)

(56) References Cited

U.S. PATENT DOCUMENTS 2,524,337 A * 10/1950 Whittaker ............ A61B 17/122
606/120
3,106,919 A * 10/1963 Churchville ......... A61B 17/122
606/120
(Continued)

FOREIGN PATENT DOCUMENTS

WO    WO 98/48700    11/1998

OTHER PUBLICATIONS

International Search Report for PCT/US12/29965.

*Primary Examiner* — David C Eastwood
(74) *Attorney, Agent, or Firm* — Edna Vassilovski (57) ABSTRACT

Provided is a jaw tool formed from two separable units and which includes a fastening device that attaches the two units together when the jaw tool is in use and which may automatically separate the units after the device performs its function such as clamping and/or cutting. Also provided is a jaw tool having a cutting blade wherein the contours of the device are shaped so that force is concentrated on the cutting bade when the device is closed. The jaw tool may be manufactured from a single injection molded-component that is used in duplicate to form the jaw tool. The jaw tool may be used in various applications in which it may be beneficial to simultaneously clamp and cut an object, such as various medical applications including vascular, gastrointestinal, respiratory, and placental.

16 Claims, 7 Drawing Sheets

(52) U.S. Cl.
CPC ............... *A61B 2017/00526* (2013.01); *A61B 2017/00858* (2013.01); *A61B 2017/1225* (2013.01); *Y10T 29/49826* (2015.01)

(58) Field of Classification Search
CPC ..... A61B 17/1285; A61B 17/08; A61B 17/12; A61B 17/10; A61B 17/3201; A61B 17/3205; A61B 17/2931; A61B 17/28; A61B 17/2804; A61B 2017/2808; A61B 17/2816; A61B 17/282; A61B 2017/2825; A61B 17/2833; A61B 2017/2837; A61B 2017/2906; A61B 2017/2908; A61B 2017/2926; A61B 2017/2931; A61B 2017/2946; A61B 2017/2947; A61F 6/20
See application file for complete search history.

(56) References Cited

U.S. PATENT DOCUMENTS

| | | | | |
|---|---|---|---|---|
| 4,716,886 A | * | 1/1988 | Schulman | A61B 17/122 30/124 |
| 4,938,215 A | * | 7/1990 | Schulman | A61B 17/122 30/124 |
| 5,462,555 A | * | 10/1995 | Bolanos | A61B 17/122 606/120 |
| 5,584,840 A | * | 12/1996 | Ramsey | A61B 17/122 606/120 |
| 5,667,516 A | * | 9/1997 | Allen | A61B 17/122 606/120 |
| 5,676,672 A | * | 10/1997 | Watson | A61B 17/122 606/120 |
| 5,817,103 A | * | 10/1998 | Bell | A61B 17/122 606/120 |
| 5,913,862 A | * | 6/1999 | Ramsey | A61B 17/122 606/120 |
| 6,348,057 B1 | * | 2/2002 | Porat | A61B 17/122 606/120 |
| D455,832 S | | 4/2002 | Watson et al. | |
| 6,443,958 B1 | * | 9/2002 | Watson, Jr. | A61B 17/122 606/120 |
| 8,496,668 B2 | * | 7/2013 | Rice | A61B 17/122 30/134 |
| 2003/0074009 A1 | | 4/2003 | Ramsey et al. | |
| 2010/0137877 A1 | * | 6/2010 | Rice | A61B 17/122 606/120 |
| 2011/0054489 A1 | * | 3/2011 | Pan | A61B 17/122 606/120 |
| 2014/0076955 A1 | * | 3/2014 | Lorenz | A61B 17/29 227/176.1 |

* cited by examiner

MULTI-COMPONENT DETACHABLE JAW TOOLS AND METHODS OF USING AND MAKING SAME

CROSS-REFERENCE TO RELATED APPLICATIONS

This application is a National Phase entry under 35 U.S.C. Section 371 of PCT Application No. PCT/US12/29965, filed on Mar. 21, 2012, entitled "MULTI-COMPONENT DETACHABLE JAW TOOLS AND METHODS OF USING AND MAKING SAME", which claims benefit of priority under 35 U.S.C. §119(e) to U.S. Provisional Patent Application No. 61/465,564, entitled, "SEPARATING MECHANISM AND GRIP FOR CLAMPING DEVICE," filed Mar. 21, 2011. The foregoing PCT application and provisional application are incorporated herein by reference in their entirety.

FIELD

Generally, this specification relates to multi-component jaw tools with separable parts, methods of using the jaw tools, and methods of making the jaw tools. More specifically, this specification relates to multi-component jaw tools with locking devices that engage to fasten components of the jaw tool together and automatically disengage when the jaw tool moves from an open-jaws position to a closed-jaws position.

BACKGROUND

Infections represent one of the most common complications of childbirth. Even in developed countries, individual cases and epidemics of cord infections continue to occur such as in births outside of hospital settings. In developing nations where health care infrastructure is commonly limited, most deliveries occur outside a hospital setting with help from family or birth attendants. Two-thirds of neonatal deaths worldwide occur in developing countries, where traditional birth practices involve severing the cord using non-sterile instruments that often lead to infection. This is due not only to poor access to healthcare but also socio-cultural behaviors. In many cultures, some type of ritual substance is applied to the cord stump. Ash, oil, butter, spice pastes, herbs, mud, and cow or chicken dung are commonly used, and they are often contaminated with bacteria and spores. This practice of applying substances to the cord is most commonly employed to prevent bleeding, to promote separation of the stump, and to keep spirits away. With such unsanitary conditions, there exists a much higher rate of infant mortality due to preventable causes, such as bacterial infections and neonatal tetanus. The lack of research efforts targeted at birth conditions outside of hospitals in developing nations has simultaneously prevented the development of effective, affordable, and feasible preventative strategies that could be widely applied towards neonatal health.

The first few weeks of a newborn mammal's life are critical to its long-term survival and health. Umbilical cord care is just as important in veterinary use as it is in human use, especially since the environment an animal is born into is usually less sterile than that of a human birth. The umbilical cord is usually severed immediately after a birth, and typically a disinfectant is applied to prevent pathogens from entering an animal's body through the cord. Umbilical cord devices are rarely used in veterinary medicine, even though they could be equally as beneficial in helping to prevent infection. Large animal births, in particular, could benefit from an improved means of severing, disinfecting, and covering the umbilical cord, as many large animal births are not attended by a trained veterinarian but by a livestock handler.

Currently, there is limited support for research that focuses on the preventable causes of neonatal infection and death. A key disadvantage of the present umbilical cord cutting method is its multi-step nature; the procedure of severing the umbilical cord involves three pieces of equipment: two clamps and a cutter. In practice, two metal clamps are secured to the umbilical cord in a spaced relation to one another, and the cord is then cut between the two clamps using scissors. The metal clamp on the baby's side is then replaced with a plastic clamp and the other is removed when the placenta is discarded. Outside of the hospital, the method for severing the umbilical cord often involves the use of tying devices, usually a type of string, to stop the flow of blood and a sharp blade, often contaminated, to sever the cord between the two points. Additionally, cutting the cord at an intermediate distance between two clamps leaves an edge of the cord past the clamp, which is a prime site for infection.

Various surgical instruments have been developed to separate and clamp the umbilical cord joining a newborn infant and the mother. However, most are reusable, which presents additional health concerns due to the possibility of contamination and infection; those that claim not to be reusable still utilize a metallic cutting device that could be easily removed and reused. The metallic blade is problematic for three reasons: it is a safety hazard, there is a risk of the blade being removed for reuse, and it is less economical to manufacture and distribute. In addition, variations on obstetric scissors do not provide adequate protection from blood splatter, placing the birth attendant at risk from contracting Hepatitis B, Hepatitis C, and HIV. Furthermore, it is usually necessary to first orient the device so that the clamp side with the blade remains on the mother's side of the cord to be discarded with the placenta. Improper orientation of such devices is more likely to occur in developing nations because language barriers will limit the effectiveness of providing instructions for proper use. This type of mistake may leave the wrong side of the device with the newborn, possibly resulting in infection and various other complications.

Some umbilical clamps include two parts, a maternal-side clamp and an infant-side clamp which are aligned and joined during the clamping procedure and separated after the clamping procedure. U.S. patent application Ser. No. 12/506,799 describes such a device and is hereby incorporated by reference in its entirety.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

SUMMARY

The present disclosure relates to jaw tools having separable components and one or more lock mechanisms, which lock mechanisms engage to join together at least two of the separable components of the jaw tool when the jaw tool is in a first position, for example in an open-jaws position, and which lock mechanisms automatically disengage when the jaw tool moves to a second position, for example a closed-jaws position, or for example a fully closed-jaws position. In some embodiments, at least one of the one or more lock mechanisms is configured to automatic ally cause the at least two separable components to disengage from one another (at least partially) when the lock mechanism disengages. In some embodiments, at least one of the one or more lock mechanisms is configured to also keep the upper jaw and lower jaw (a jaw is also referred to as a "working member" herein) in a closed position after the tool moves from an open-jaws position to a fully closed-jaws position. In some embodiments, the tool also includes a fail-safe device that permits manual disengagement of at least one of the lock mechanisms if it fails to automatically disengage. In some embodiments, the fail safe device is an aperture that provides access to the at least one lock mechanism, enabling a user to break or release (deflect) a resilient latch or receiving aperture thereby disengaging the lock mechanism.

In some embodiments, the jaw tool includes a first and a second separable component (two components which may be aligned and reversibly joined together to form the jaw tool) and a lock mechanism, wherein each component includes a first working member hingedly connected to a second working member to form a set of jaws, and a portion of the lock mechanism, wherein when the two separable components are aligned and the tool is in an open-jaws position, the portion of the lock mechanism on the first component engages the portion of the lock mechanism on the second component to join the two separable components together and form a jaw tool having a unitary first working member and a unitary second working member forming a set of unitary jaws, and further wherein the portion of the lock mechanism on the first component disengages from the portion of the lock mechanism on the second half component the jaw tool is in the closed-jaws position, for example a fully closed-jaws position.

In some embodiments, the jaw tool includes a first and a second separable component and at least two lock mechanisms, wherein each separable component has a jaw comprising a first working member hingedly connected to a second working member and a portion of each of the two lock mechanisms, and further wherein when the two components are aligned and each separable component is in an open-jaws position, the portion of the at least two lock mechanisms on the first component engage the portion of the at least two lock mechanisms on the second component to join the two separable components together to form a jaw tool with a set of unitary jaws, and the portion of the lock mechanisms on the first separable component disengages from the portion of the lock mechanisms on the second separable component when the jaw tool moves from an open-jaws to a closed-jaws position, for example a fully closed-jaws position. In some embodiments the working faces of the jaws provide a cutting and/or clamping surface, and the lock mechanisms may also contribute to the structural integrity of the device and stability of the working surfaces (cutting and/or clamping surfaces) by holding the separable components in rigid alignment. In further embodiments, the jaw tool includes additional structure for insuring alignment between the separable components and/or for providing a stable cutting and/or clamping surface, which may be, for example, pegs and peg-receiving apertures, wherein pegs on the first component can be inserted into corresponding peg-receiving apertures on the second component and vice versa.

In some embodiments, the jaw tool includes a first and a second separable half and at least a first and a second lock mechanism, wherein each half has a set of jaws comprising a first working member hingedly connected to a second working member and each half also has a portion of the at least first lock mechanism and a portion of the at least second lock mechanism, and when the halves are aligned and each set of jaws is in the open-jaws position, the portion of the at least first lock mechanism on the first half engages with the portion of the at least first lock mechanism on the second half and the portion of the at least second lock mechanism on the first half engages with the portion of the at least second lock mechanism on the second half thereby joining the two separable halves to form a set of unitary jaws, and wherein the at least two lock mechanisms also automatically disengage when the jaw tool is in the closed-jaws posit ion, for example the fully closed-jaws position, and further wherein at least one of the at least first or at least second lock mechanisms on each half also automatically engages to maintain the jaws on each of the first and the second separable half in a closed position when the tool is moved to the closed-jaws position, for example the fully closed-jaws position.

In some embodiments, the jaw tool comprises first and second separable halves, wherein each half has the same shape such that the jaw tool is made by essentially fastening two first separable halves together (i.e. the second se parable half is a second first separable half). In some embodiments the first and second separable halves have the same shape, and the halves are configured such that they can be produced from the same sets of molds. In further embodiments, the first and second separable halves are the same, and the halves are configured such that they can be produced from the same single mold. In yet further such embodiments, each half includes a first working member and second working member in hinged connection forming a set of jaws and one or more integral lock mechanisms, such that the one or more integral lock mechanisms on the first half engage with the corresponding one or more integral lock mechanisms on the second half to join the two separable halves together when the jaw tool is in the open-jaws position, and the one or more integral lock mechanisms automatically disengage when the jaw tool is in the closed-jaws position. In other embodiments, at least one of one or more integral lock mechanisms on each half also automatically locks the jaws on each half in a closed-jaws position when the tool is moved to the closed-jaws position, for example the fully closed-jaws position. In further embodiments, the first and second separable halves are mirror images of one another.

In some embodiments, the jaw tool includes: first and second separable components and a lock mechanism, wherein each of the separable components has an inner side and an outer side opposite the inner side (the inner sides of each separable component face each other when the components are aligned to be joined) and a set of jaws including first and second working members in hinged connection, and, further wherein the lock mechanism includes a j-shaped protuberance, a lipped aperture, and a release pin on each of the first and second separable components, the j-shaped protuberance extending substantially laterally from the inner side of a working member of a separable component, the lipped aperture being located on the other working member on the same separable component and in vertical alignment with the j-shaped protuberance, and the release pin being located on the same working member as the j-shaped protuberance and extending toward the other working member of the separable component such that the j-shaped protuberance on one of the separable components resiliently engages with the lipped aperture on the other separable component to lock the components together when the jaws are in an open-jaws position, and when the jaws move to a closed-jaws position the release pin applies a biasing force to the j-shaped protuberance releasing it from the lipped aperture.

In some embodiments, the jaw tool includes: first and second separable components and a lock mechanism. In some embodiments, the separable components have a first working member and a second working member hingedly connected to one another, an inner side and an opposite outer side, and a back end and a front end, the inner side being the side facing the other separable component when the components are aligned to be joined, and the back end being the hinge end. In further embodiments, the lock mechanism is located at the front end of each separable component and includes a j-shaped resilient lever for locking the first working member and the second working member together, a notched resilient lever for locking the first and second separable components together, a release pin and a lipped aperture, wherein the j-shaped lever and notched lever are both located on one of the first or second working members with the j-shaped lever being located toward the outer edge relative the notched lever such that the notched lever on one of the separable components can engage with the notched lever on the other separable component locking the components together, and the lipped aperture and the release pin are both located on the other working member with the lipped aperture being aligned to engage the j-shaped protuberance when the jaws close to maintain the jaws in a closed position and the release pin being aligned with the notched lever such that when the jaws close the release pin applies a biasing force to the notched lever causing it to disengage from its counterpart notched lever on the other component.

In some embodiments, the jaw tool comprises a first and second separable half and a lock mechanism that locks to join the two separable halves together when the jaw tool is in the op en jaws position and automatically unlocks when the jaw tool is in the closed-jaws position, and the jaw tool further includes a grip that distributes force in the center of the device when pressure is app lied to move the jaws from the open-jaws position to the closed-jaws position. In further embodiments, the jaw tool grip guides the object providing force to the center of the device. In some embodiments, the jaw tool grip distributes force to the point of separation of the two units. In some embodiments, the jaw tool has a grip that slants such that when the units are locked together, the grip is in a V-shaped groove directing fingers between the two units.

The present disclosure also relates to methods of using multi-component jaw tools having separable parts. In some embodiments, the jaw tools are used to cut and/or clamp an object. In some embodiments, the jaw tools may be used in surgical procedures, for example surgical procedures requiring clamping and/or cutting tissue. In some embodiments, the methods of using the jaw tools includes: fastening together two separable components of a jaw tool using a latch while the jaw tool is in the open-jaws position; placing an object, such as hum an or animal tissue, to be cut in the tool between opposing faces (i.e. working faces) of the jaw; closing the jaw on the object causing the tool to clamp and/or cut the object, wherein the latch is automatically unfastened when the jaw reaches the closed position, and disengaging the separable components one from the other.

The present disclosure also provides a method of manufacturing a surgical tool, which includes injection molding parts of a first plastic half, assembling the first plastic half in duplicate, and packaging or combining two first plastic halves together to form the surgical tool, wherein the first plastic half includes a set of jaws and an integral lock mechanism that when combined with the lock mechanism on a second first plastic half fastens the two first plastic parts together to form a tool with a set of unitary jaws when each of the first plastic parts is aligned and in the open-jaws position and unfastens the lock mechanism on each of the two first plastic halves when the tool is in a closed-jaws position. In further embodiments, the method of manufacturing includes injection molding a first plastic half using only a single mold, and packaging or combining two first plastic halves together to form the surgical tool, wherein the first plastic half includes a set of jaws and an integral lock mechanism that when combined with the lock mechanism on a second first plastic half fastens the two first plastic parts together to form a tool with a set of unitary jaws when each of the first plastic parts is aligned and in the open jaws position and unfastens the lock mechanism on each of the two first plastic halves when the tool is in a closed-jaws position. In further embodiments, the method also includes, after injection molding the first plastic part and/or assembling the first plastic part, aligning two of the first plastic parts to form a tool having a set of unitary jaws; fastening the two first plastic parts together with the integral lock mechanism when each of the first plastic parts is aligned and in an open jaw position.

While the disclosure provides certain specific embodiments, the invention is not limited to those embodiments. A person of ordinary skill will appreciate from the description herein that modifications can be made to the described embodiments and therefore that specification is broader in scope than the described embodiments. All examples are therefore non-limiting.

DETAILED DESCRIPTION

Detailed descriptions of one or more embodiments are provided herein. It is to be understood, however, that the present invention may be embodied in various for ms. Therefore, specific details disclosed herein are not to be interpreted as limiting, but rather as a basis for the claims and as a representative basis for teaching one skilled in the art to employ the present invention in any appropriate manner.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

Where ever the terms "a" or "an" are used, "one or more" is understood, unless such interpretation is nonsensical in context.

The phrase "an open-jaws position" is understood to mean any open position of a jaw tool, and does not necessarily imply that the jaw tool is open to its fullest extent. Similarly, the phrase "a closed-jaws position" does not mean that the jaw is fully closed.

For purposes of this application, the phrase "auto-disengageable lock mechanism" is a device that engages to fasten together at least two components of a multi-component jaw tool and also automatically disengages when the jaw tool moves from an open-jaws to a closed-jaws position. "Auto-disengageable lock mechanisms" are also referred to simply as "lock mechanisms" as clarified in context.

The term "unitary" when used to describe an element of the jaw tool means that while the element may be comprised of separable components, it functions as a single component. For example a set of "unitary jaws" refers to jaws formed by attaching one set of jaws to another set of jaws to effectively form a (wider), single set of jaws. For example, according to some embodiments herein, the jaw tool includes separable halves, and each half has a set of jaws comprising a first working member hingedly connected to a second working member. When the halves are aligned and attached together, the two first working members form a "unitary first working member" and the two second working members form a "unitary second working member" resulting in the two sets of jaws forming a "unitary set of jaws."

Parts which are in "hinged connection" or "hingedly connected" together or the like means that the parts can move over a range of angles relative to one another; it does not mean that a separate hinge is necessarily required. As one example, the parts may be molded together and include a narrower section between the parts permitting them to flex relative to one another.

The disclosure provides jaw tools having separable components, wherein the components are fastened together by a lock mechanism which engages when the tool is in a first position, for example an open-jaws position, and which disengages when the tool is in a second position, for example a closed-jaws position. For example, in some embodiments, the separable components are a first part comprising a first set of jaws and a second part comprising a second sets of jaws and the lock mechanism attaches the first part to the second part such that the first set of jaws and the second set of jaws combine to form a single set of unitary jaws, wherein the lock mechanism engages when the first set of jaws and the second set of jaws (or the combined unitary jaws) is in an open-jaws position and disengages when the set of unitary jaws moves from an open-jaws positions to a closed-jaws position. In some embodiments, the separable components of the jaw tool are attached together by the lock mechanism when the tool is in the first position, for example, an open jaws position, and the components automatically detach from one another when the tool moves from the first position such as the open-jaws to a second position such as a closed-jaws position. In some embodiments, the separable components of the jaw tools are two symmetrical or identical separable halves such that, for example, a single set of molds can be used to produce one of the halves, which is then used in duplicate to provide the other half and together build the jaw tool. In some embodiments, the separable components of the jaw tools are two symmetrical or identical halves and a half is configured such that only a single mold is required to produce it and thereby only a single mold is required to produce both halves. This particular embodiment (identical halves) is represented in the figures and discussed in detail herein, but devices consistent with the disclosure are not limited to those having identical halves.

The disclosure also provides methods of making jaw tools having separable components. In some embodiments, the jaw tools are made by injection molding a first component having a set of jaws and a lock mechanism, and packaging two of the first components together for forming the jaw tool, wherein the lock mechanism is configured to engage with the same lock mechanism on a second first component to fasten the two components together to form a tool a set of unitary jaws when the two first components are aligned and in the open-jaws position, and is further configured to disengage from the same lock mechanism on the second first component when the tool is in a closed-jaws position. In further embodiments, the method of making a tool further includes aligning two first components together to form a set of unitary jaws, and using the lock mechanism to fasten the two first components together while in an open-jaws position.

The disclosure also provides methods of using the jaw tools, for example in medical applications wherein tissue is clamped and/or cut. In some embodiments the tissue is an umbilical cord, and the method includes placing the umbilical cord on a working face or between the faces of the jaws of a jaw tool according to the present disclosure when the jaw tool is in an open-jaws position, closing down on the umbilical cord to effect clamping and/or cutting of the umbilical cord, and separating the components of the jaw tool, for example separating the set of unitary jaws into two sets of jaws, after the umbilical cord is cut.

FIGS. 1-6 illustrate an embodiment of a jaw tool according to the disclosure, specifically an umbilical cord clamping and cutting device, which includes a front-end auto-disengageable lock mechanism and a hinge-end auto-disengageable lock mechanism. FIG. 7 illustrates another embodiment of a jaw tool according to the disclosure, specifically an umbilical cord clamping and cutting device similar to that of FIGS. 1-6 except that it also includes a release lever or tang at the front end of each separable component to maintain the jaws of each component in a closed-jaws position. In some embodiments, jaw tools according to the disclosure may include a front-end release lever or tang instead of, rather than in addition to, the front-end auto-disengageable lock mechanism.

Although the examples herein focus on an umbilical cord clam ping and cutting device, jaw tools according to the disclosure are not limited to that specific application. Rather, the jaw too is can be adapted to any application wherein a jaw tool comprising separable components (for example a jaw tool with a set of unitary jaws that separate into two sets of jaws, one set on each separable component), such as separable halves, or such as separable identical or symmetrical halves may be used or may be useful. For example, there are also vascular, gynecologic, gastrointestinal, respiratory, trauma, and agricultural applications wherein an object may be advantageously or otherwise cut and/or simultaneously clamped by a unitary jaw tool having separable components such as two separable components that join together to create the working surface (i.e. the cutting and/or clamping surface) and which are separated after the cutting and/or clamping procedure is complete. Additionally, this technology is dually suited for applications in which the device may be used laparoscopically or without dexterity provided by human hands wherein an object may be advantageously or otherwise cut and/or simultaneously clamped by a unitary jaw tool having separable components such as two separable components that join together to create the working surface (i.e. the cutting and/or clamping surface) and which are separated after the procedure is completed with force only applied unidirectionally. More specifically, although not limited, the technology could be leveraged for laparoscopic fallopian tube ligations, cholecystectomies requiring vascular and/or biliary ligation, or any other non-specific tissue, vascular, lymphatic, or biliary ligation Referring now to FIG. 1, an embodiment of a jaw tool 10, specifically an embodiment of an umbilical cord cutting and clam ping device, in accordance with the present disclosure is shown in perspective view from the front end 20 (also referred to herein as the distal end) in an open-jaws position. Jaw tool 10 has a first unitary working member 30 and a second unitary working member 40 connected by a unitary hinge 50 to form a set of unitary jaws 25. Although a unitary hinge 50 is shown, any structure that enables the first unitary working member 30 to flex across a range of angles in a given plane relative to the second unitary working member 40 to create jaw movement may be used, for example as represented in FIG. 7 by the integral, flexible molded hinge 51. The working members 30, 40 provide working surfaces 85. As is better shown in FIG. 3, the working surfaces 85 have a slight curvature, such as a convex curvature on one working member of the set of jaws and a corresponding concave curvature on the other working member of the set of jaws, permitting, for example, umbilical tissue to spread out along the working surfaces (cutting and clamping surfaces) 85.

Figure 2:
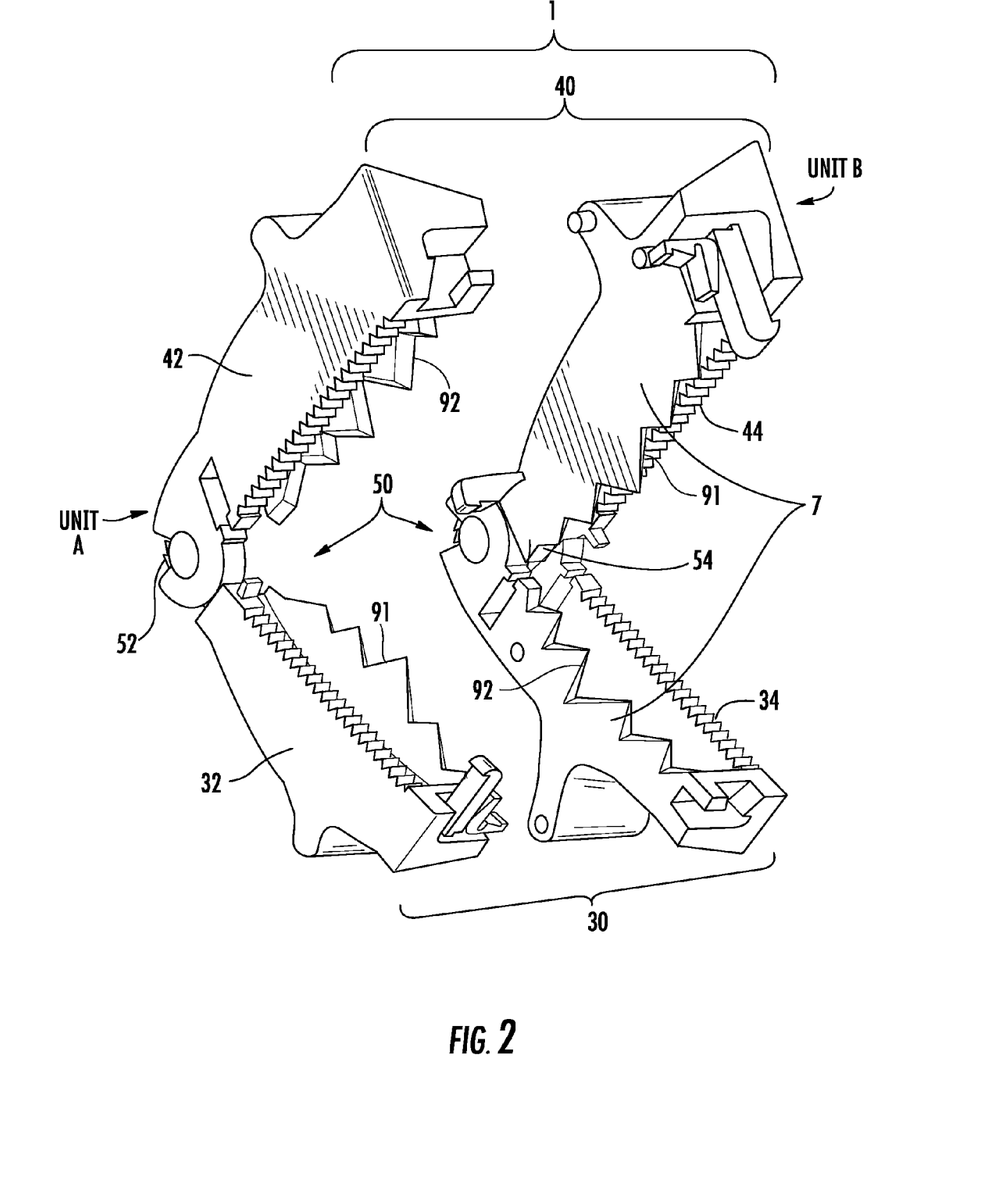
FIG. 2 is a front-end perspective of the jaw tool embodiment of FIG. 1, where the components are separated and are each in an open position.
Figure 3:
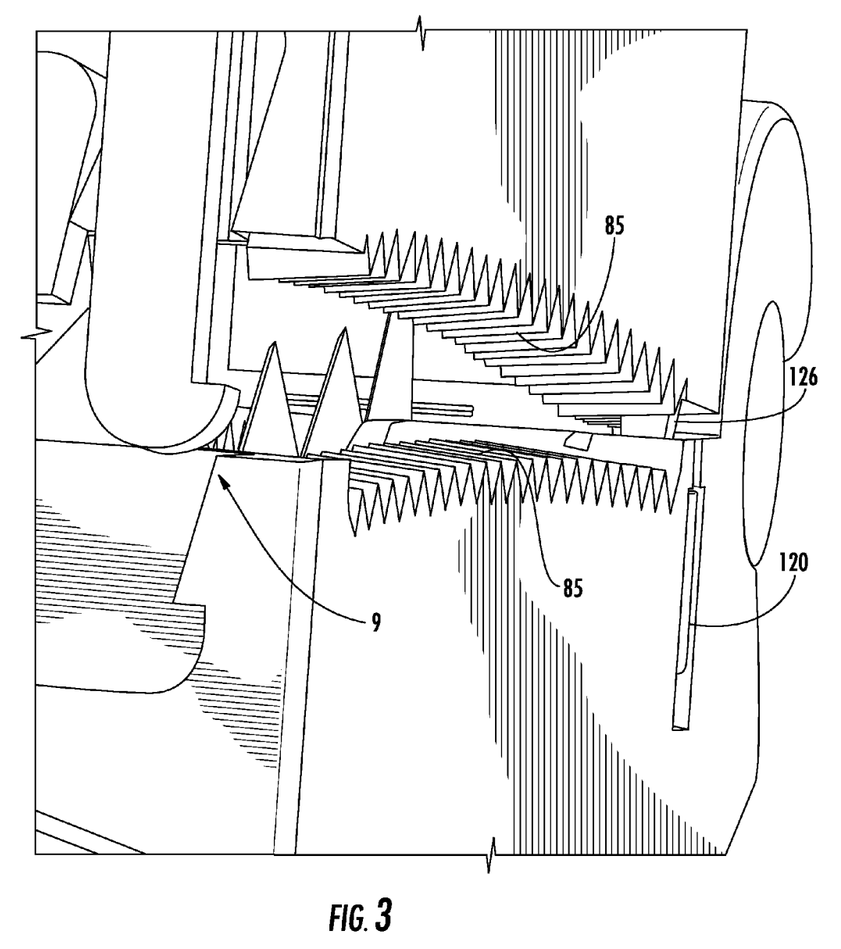
FIG. 3 is a close up perspective view of a portion of the front end lock mechanism and the working surface of the embodiment of FIG. 1.

As is better shown in FIG. 2, the jaw tool 10 is formed from two separable components, referred to herein as Unit A and Unit B. In the illustrated embodiment, Unit A and Unit B are identical. However, the jaw tools according to this disclosure are not limited to those having identical halves. For purposes of this disclosure "identical" means that the components or parts of one Unit could be produced from the same mold (or molds) as the components or parts of the other Unit, if they were manufactured, for example, by injection molding. Thus, first unitary working member 30 is comprised of a first working member 32 on Unit A and a first working member 42 on Unit B, which abut one another in use. Similarly, second unitary working member 40 is comprised of a second working member 34 on Unit A and a second working member 44 on Unit B, which also abut one another in use. So too, the unitary hinge 50 is also comprised of two separate hinge portions, a first hinge portion 52 on Unit A and a second hinge portion 54 on Unit B.

Referring back to FIG. 1, the jaw tool 10 also includes optional features such as a V-shaped groove 60, an ergonomically designed grip 70, working surfaces 85 with chamfered edges 80, a central cutting blade 90, and a ratcheting mechanism (not shown) for the hinge 50. The V-shaped groove 60 distributes force to the center of the device, where the cutting blade is located, during operation. For umbilical cord applications, this may lead to more efficient severing of the umbilical tissue and may prevent twisting and deformity of the clamping device. Similarly, beyond umbilical cord applications, a V-shaped groove may lead to more efficient severing of the object to be cut, such as tissue, generally. The ratcheting mechanism prevents the jaw tool 10 from reopening once closed. As a person of skill in the art would appreciate from the disclosure herein, not all jaw tool embodiments within the scope of the disclosure include a V-shaped groove 60 or the specific working surfaces described such as having a curvature and/or chamfered edges 80 and a central unitary cutting blade 90, and/or the particular illustrated grip 70. For example, a multi-component detachable jaw tool according to this disclosure for use in arthroscopic or laparoscopic applications may have a groove or other method for attachment to a separate tool (e.g. Laparoscopic instrument) to grip the multi-component detachable jaw tool rather than a protruding grip.

Similarly, a person of skill would also appreciate from the disclosure herein that the functions each exemplary structure provides can alternatively be provided by other structures. FIG. 7 illustrates an embodiment of an alternative structure (which can be used instead of or in addition to the hinge ratcheting mechanism) for preventing the jaw tool from reopening once it is closed. Specifically, one of the first or second working members 30, 40 includes a flexible tang 130 (or, for example, a tang that is pivotably or hingedly connected to one of the first or second working members 30, 40) at its front end 20. The other working member has a notch or lip 140 which engages with the tang 130 locking the jaws on a given Unit (the first working member and the second working member on the given Unit), for example locking together the jaws 42 of Unit A (e.g. locking together the first working member 32 and the second working member 34 of Unit A) in a closed position, for example a fully-closed position. A downward or appropriate directional force on the tang 130, for example by a user's thumb, releases the tang 130 from the lip 140 permitting the jaws on the given Unit to be reopened. The jaw tool embodiment of FIG. 7 also illustrates an alternative embodiment of a hinge 51 for hingedly connecting the first working member 30 to the second working member 40. The hinge 51 is flexible, and integrally molded to the Unit such that when the tang 130 is released, the jaws spring open.

In some embodiments, jaw tools having flexible tang locking devices and hinges such as shown in FIG. 7 may include the flexible tang locking device on only one of the pair of separable halves. This may be useful in the delivery room, for example, if the doctor wishes to temporarily unclamp the umbilical cord on the placental side to collect blood and then re-latch the jaws after collecting the blood sample.

As described above, the working surfaces 85 include chamfered edges 80 and a cutting blade 90. As is better shown in FIG. 2, the outer edge of the working members provides the chamfered edges 80 and the inner edge of the working members contains a saw tooth cutting blade. When the inner edges of each of Unit A and Unit B are aligned and joined to form the jaw tool 10, a unitary saw tooth cutting blade 90 is formed. In the embodiment shown, the saw tooth cutting blade of each Unit includes a first cutting blade 91 and a second cutting blade 92, which are hingedly connected. The first cutting blade 91 includes one or more teeth that are taller than any of the teeth on the second cutting blade 92 resulting in the first cutting blade 91 having a taller profile than the second cutting blade 92. The teeth on each of the first 91 and second 92 cutting blades are configured to receive one another when the Unit is in a closed position. Consequently, when Unit A and Unit B are joined together forming a unitary saw tooth cutting blade 90, the upper half is formed from the juxtaposition of a first cutting blade 91 and second cutting blade 92 and so has a side with taller teeth and a side with shorter teeth. Similarly, the lower half of the unitary saw tooth cutting blade 90 is formed from the juxtaposition of a first cutting blade 91 and a second cutting blade 92 therefore also resulting in a a side with taller teeth and a side with shorter teeth. Further, as is evident in FIG. 2, in the illustrated embodiment, when Unit A and Unit B are joined, the taller, first cutting blade 91 is on the lower half of Unit A but is on the upper half of Unit B. Such a configuration, wherein each of the upper and lower halves of the unitary saw tooth cutting blade 90 are comprised of sides with taller and shorter teeth, with the taller teeth being on the upper half of one of the Units and the lower half of the other of the Units, results in sheer force when in use which assists in cutting tissue.

Figure 4:
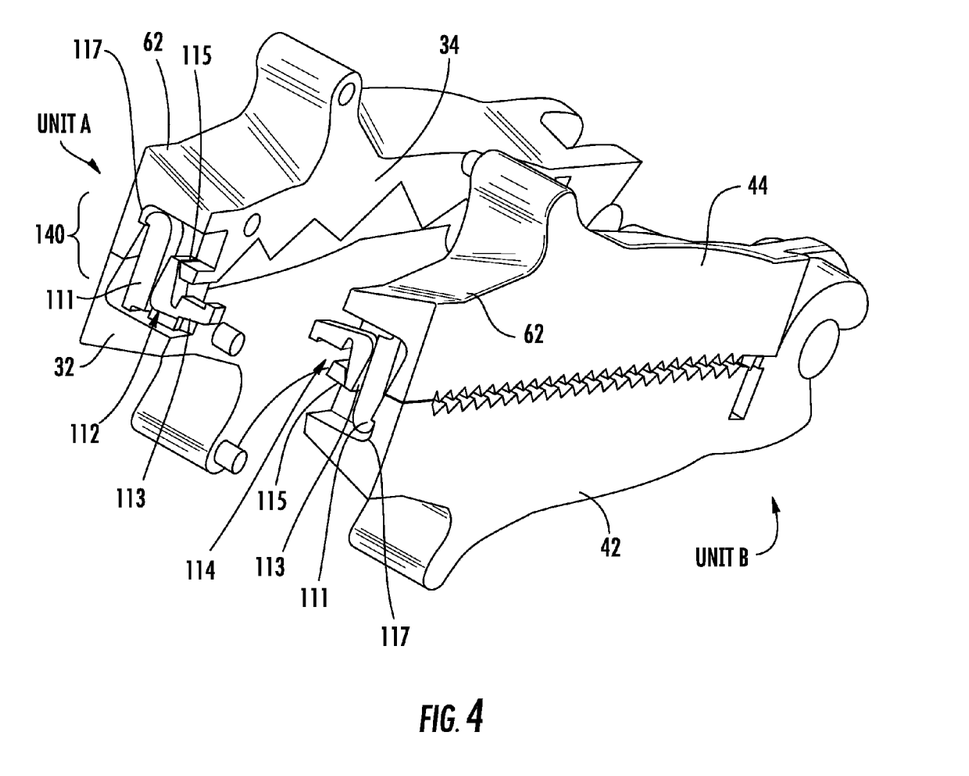
FIG. 4 is a front-end perspective view of the embodiment of FIG. 1, where the two parts have been separated and are each in a closed position.

As can be seen in FIG. 4, the V-shaped groove 60 is created when slanted surface 62 on each of Unit A and Unit B are aligned and combined when Unit A and Unit B are fastened together to form jaw tool 10.

Jaw tool 10 also includes a two lock mechanisms 110, 120. As is better shown in FIG. 4, a portion 112 of lock mechanism 110 is integral with Unit A and a portion of 114 of lock mechanism 110 is integral with Unit B. Similarly, as better seen in FIG. 5, a portion 122 of lock mechanism 120 is integral with Unit A and therefore (because in the illustrated embodiment Unit A and Unit B are identical) a portion (not shown) of lock mechanism 120 is integral with Unit B. For purposes of this disclosure, the phrase "lock mechanism" refers either to the portion of the fastening device on each of Units A or B or to the fastening device in its entirety (both portions collectively) as will be apparent from context. Thus, portions 112, 114, 122 (and the portion of lock mechanism 120 on Unit B, which is not shown) are referred to simply as "lock mechanisms."

Figure 1:
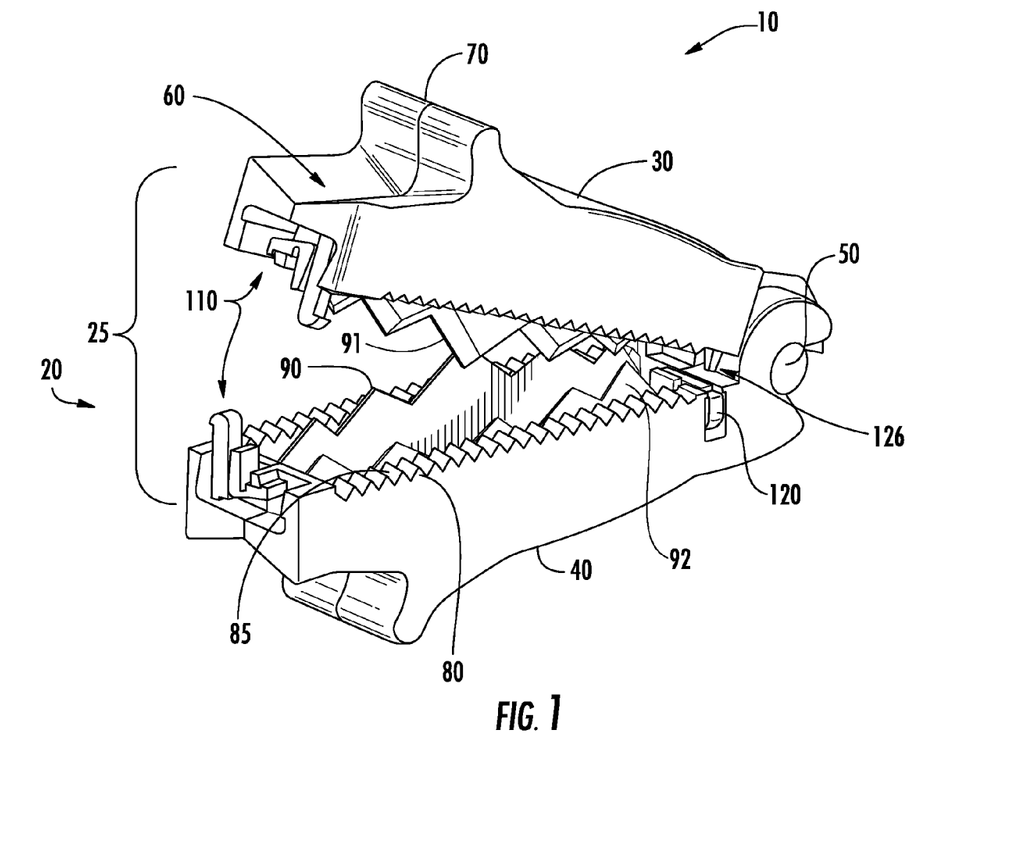
FIG. 1 is a front-end perspective view of an embodiment of a two-part jaw tool in an open position and in which the two parts are fastened together.

Referring back to FIG. 1, the lock mechanisms 110, 120 flank the working surfaces of the jaw tool 10 so as not to interfere with the clamping and cutting action of the jaw tool 10. Other jaw tool embodiments within the scope of this disclosure may have only one lock mechanism or may have more than two lock mechanisms. For example, in some embodiments such as in certain applications wherein a device smaller than a typical umbilical cord clamp may be used such as in arthroscopic applications, or wherein it may be beneficial, the jaw tool may have only one lock mechanism. As another example, in some embodiments, the jaw tool may have one or more "auto-disengageable" lock mechanisms (a lock mechanism that engages to fasten separable components together while also automatically disengaging when the jaw tool moves from an open-jaws position to a closed-jaws position) and may have one or more lock mechanisms that manually disengage. For example, an umbilical cord clamping and cutting device may be as shown in FIG. 1, except that front lock mechanism 110 is replaced with a manually releasable tang as shown in FIG. 7. (Embodiments according to the disclosure may also include a front-end auto-disengageable lock mechanism in addition to the manually releasable tang of FIG. 7, for example because the auto-disengageable lock mechanism primarily serves to fasten and unfasten the two Units together, whereas the releasable tang serves to lock the jaws in a closed position.)

FIG. 4 provides a better view of front-end lock mechanism 110, which is an embodiment of an auto-disengage able lock mechanism. As can be seen, in the particular embodiment, the portion 112 of lock mechanism 110 on Unit A is the same as the portion 114 of the lock mechanism 110 on Unit B. Specifically, each lock mechanism 112, 114 includes two latches (in the particular embodiment, the latches are a j-shaped resilient lever 111 and a notched l-shaped resilient lever 113), a release pin 115, and a lipped or notched aperture 117. The j-shaped resilient lever 111 and notched l-shaped resilient lever 113 are co-located on the same working member (in this case first working member 32 of Unit A and first working member 42 of Unit B), whereas the release pin 115 and lipped aperture 117 are co-located on the other working member (in this case second working member 34 of Unit A and second working member 44 of Unit B).

The notched l-shaped resilient lever 113 on one working member (e.g. Unit A) is shaped to receive and engage with the release pin 115 on the other working member (e.g. Unit B), locking the two halves together to form a set of unitary jaws 25. Consequently, the notched l-shaped resilient lever 113 is positioned to the inside (i.e. the side facing Unit B when the units are aligned to join together to form jaw tool 10) of the j-shaped resilient lever 111 so that it is accessible to engage with the corresponding release pin 115 on Unit B when the units are aligned to form a jaw tool 10.

The release pin 115 on a given working member (e.g. Unit A) is vertically displaced from the notched l-shaped resilient lever 113 on the same working member (e.g. Unit A) such that in operation, the release pin 115 contacts and applies a biasing force to the notched l-shaped resilient lever 113 causing it to deform (deflect) and disengage from the corresponding release pin 115 on Unit B, when the jaws 140 move from an open-jaws position to a closed-jaws position. The lipped aperture 117 on a given working member (e.g. Unit A) is vertically displaced relative to the j-shaped resilient lever 111 on the same working member (e.g. Unit A) such that, in operation, the j-shaped resilient lever 111 locks into the lipped aperture when the jaws 140 move from an open-jaws position to a closed-jaws position, helping to keep the jaws 140 in a closed-jaws position.

Figure 5:
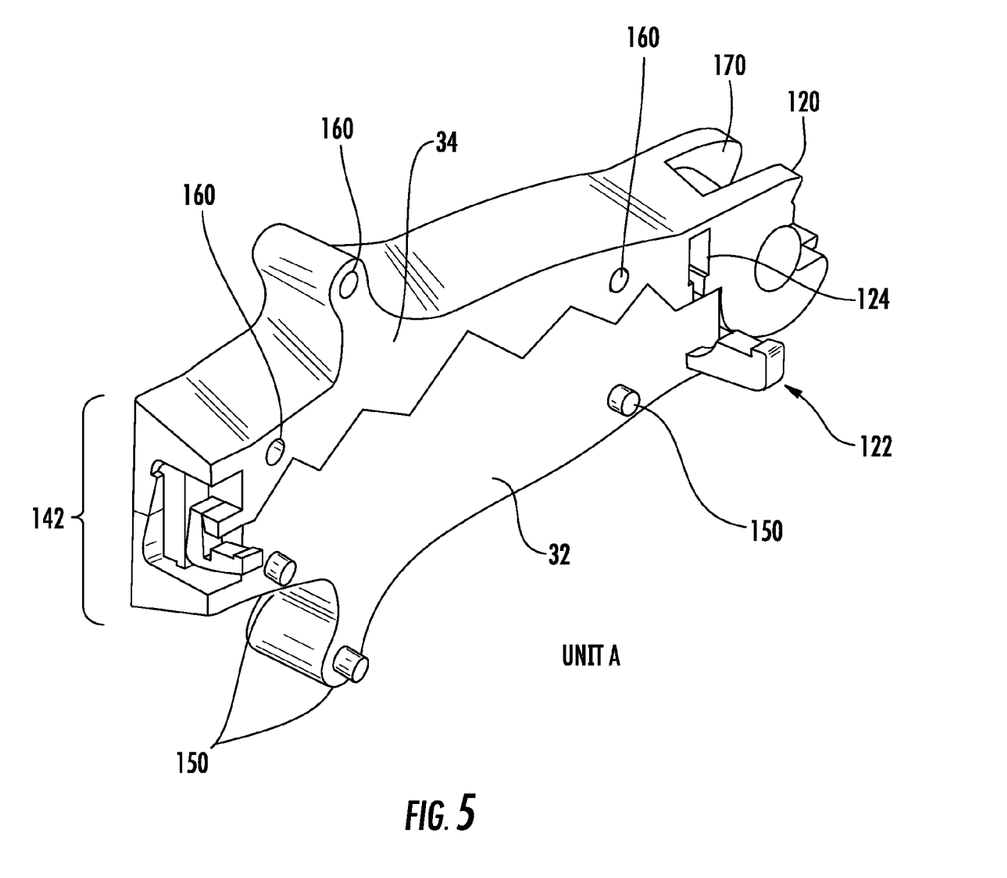
FIG. 5 is a front-end perspective view of one of the parts of the two-part jaw tool of FIG. 1 in a closed position.

FIG. 5 provides a view of back-end lock mechanism 120, which is also an embodiment of an auto-disengageable lock mechanism. Back-end lock mechanism 120 includes a latch (in the illustrated embodiment, the latch is a j-shaped protuberance 122) extending laterally beyond the plane of the inside edge of Unit A, corresponding notched receiving aperture 124, and release pin 126 (see FIG. 1). The j-shaped protuberance 122 and release pin 126 are located on one working member (either the first working member 32 or the second working member 34) and the notched receiving aperture 124 is located on the other working member. The notched receiving aperture 124 is vertically-displaced from the j-shaped protuberance 122 such that when the first separable half and the second separable half are aligned, the notched receiving aperture 124 can receive and engage the corresponding j-shaped protuberance on Unit B causing Units A and B to fasten together. The release pin 126, which may be part of the j-shaped protuberance 122, is positioned toward the outside edge relative to the j-shaped protuberance 122 such that when the jaws 142 move from an open-jaws position to a closed-jaws position, the release pin 126 contacts and applies a biasing force to the corresponding j-shaped protuberance on Unit B causing it to deform (deflect) and disengage from the notched receiving aperture 124.

Although specific examples of lock mechanisms have been described, the fastening devices or lock mechanisms can be any mechanism that maintains connection between separable components (in the illustrated embodiment halves and in specifically separable identical halves) forming a unitary jaw tool when the jaw tool is in an open position, but disengages the separable components when the jaw tool is closed, for example after the jaw tool has performed its function such as cutting and/or clamping.

FIG. 5 illustrates some additional optional elements of jaw tool 10. Whereas lock mechanisms 110, 120 assist in aligning Units A and B and rigidly holding the resulting set of unitary jaws 25, thereby also assisting in stabilizing the working surface (cutting and clamping surface), additional structure may also be provided to serve one or more of these functions. In the illustrated embodiment, pegs 150 and peg-receiving holes 160 also may assist with alignment of the two units and/or providing a stable working surface. Specifically, when Unit A and Unit B are aligned to form jaw tool 10, pegs 150 on unit A slide into corresponding peg-receiving holes on Unit B. Similarly peg-receiving holes 160 on Unit A receive corresponding pegs from Unit B.

Figure 6:
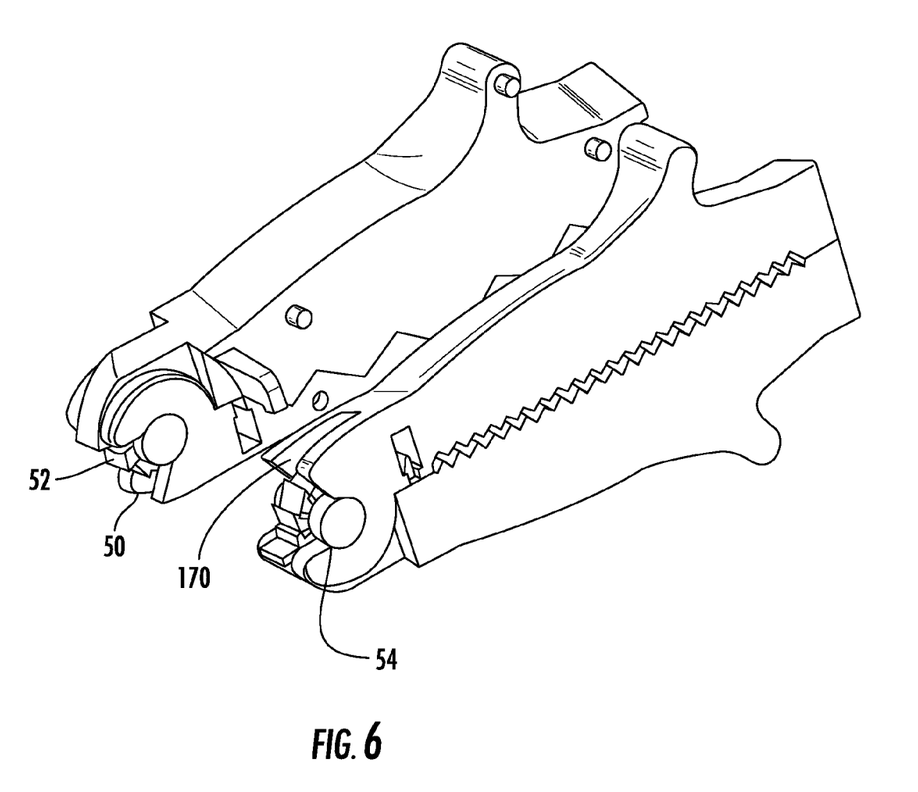
FIG. 6 is a back-end perspective view of the jaw tool of FIG. 1 with the two parts separated and each in a closed position.
Figure 7A:
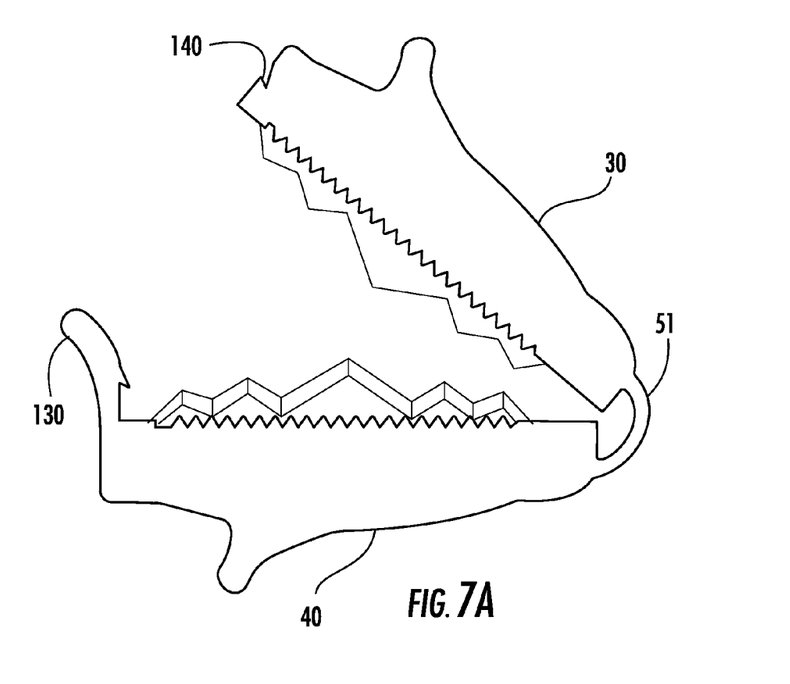
FIG. 7 is a side view of another embodiment of a multi-component detachable jaw tool according to the disclosure.
Figure 7B:
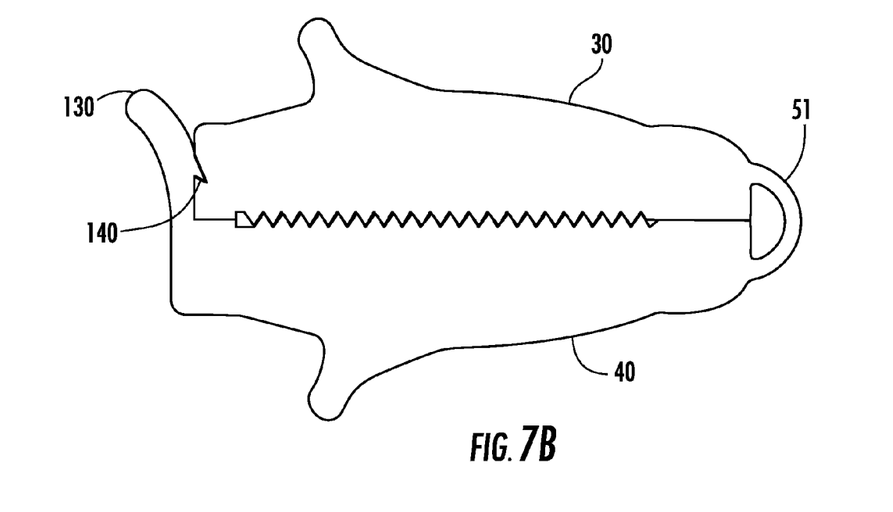

FIGS. 5 and 6 provide a view of yet another optional element of jaw tool 10, a fail-safe lock release mechanism 170. In the illustrated embodiment, the fail safe lock release mechanism 170 is an aperture located on one of the working member of a Unit, which provides access to the j-shaped protuberance engaged with the lipped aperture on the other working member of the same Unit. For example, if the release pin 126 on Unit A fails to disengage the j-shaped protuberance of Unit B, a user may insert an object into the fail-safe aperture 170 on Unit A to apply force to the j-shaped protuberance of Unit B and cause it to flex and disengage or even break off and disengage. The device has been designed so that the hinge may be disengaged in the above specified manner or any other manner necessary for correct operation of the tool as described in any iteration contained within this patent. This feature may provide safety benefits.

FIG. 6 also provides a better view of unitary hinge 50 and its separable component hinges 52, 54. A person of skill can also understand from a review of FIG. 6, that in the illustrated embodiment, an injection molded jaw tool 10 can be formed by creating only the mold or molds necessary to form Unit A. Because Unit B is the same as Unit A its components can be formed from the same mold or molds as Unit A. In some embodiments, Unit A is injection molded in two parts, specifically there is a one mold for the first working member and one mold for the second working member. Thus in some embodiments the jaw tool 10 can be formed using only two molds. In some embodiments, the hinge portion of Unit A is configured such that Unit A can be injection molded in only a single mold. Thus the jaw tool 10 can be formed using only a single mold, i.e. two Unit A components are combined to form jaw tool 10.

In operation, Unit A and Unit B are aligned with inner sides facing one another and each of Unit A and Unit B in an open-jaws position. Unit A and Unit B are fastened together by sliding pegs 150 of Unit A into peg-receiving holes 160 of Unit B, and sliding pegs 150 of Unit B into peg-receiving holes 160 of Unit A. Sliding the Units together also causes lock mechanisms 110, 120 to engage when Unit A and Unit B abut one another. Specifically the j-shaped protuberance of the back-end lock mechanism of one Unit engages with the lipped aperture on the other Unit. As well, the notched l-shaped resilient lever of the front-end lock mechanism one Unit engages with the notched l-shaped resilient lever of the other Unit. After the jaw tool 10 is assembled, a tissue (in the specific example the tissue is an umbilical cord) to be clamped and cut is placed between the working surfaces of the jaws. The jaws are then closed and the umbilical cord is simultaneously clamped (on both the placental side and the infant side) and cut. When the jaws are moved to the fully-closed position, a pin associated with each of the lock mechanisms applies a biasing force to the levers locking Units A and B together causing the levers to deflect or deform and disengage (either from the lipped aperture in the case of the back-end lock mechanism or from each other in the case of the front-end mechanism). The design of the lock mechanism also results in the two units themselves disengaging when the latches are deflected and the Units unlocked from one another. Finally, when the jaw tool is moved to the fully-closed position, a lever on each of the Units that extends form one working member to the other working member of its jaws unit (the j-shaped protuberance on the front-end lock mechanism) engages with a lipped aperture on the other working member of that jaws unit causing the jaws to remain closed at the end of the cutting/clamping procedure. The hinge on each Unit may also be ratcheted down to prevent reopening of the jaws.

A number of embodiments have been described by a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

What is claimed is:

1. A tool, comprising:
   a. a first set of jaws comprising a first cutting blade;
   b. a second set of jaws comprising a second cutting blade, wherein the first set of jaws and the second set of jaws are identical; and,
   c. a lock which attaches the first set of jaws to the second set of jaws such that the first set of jaws and the second set of jaws form a single set of unitary jaws comprising a central unitary cutting blade, wherein the lock engages when the set of unitary jaws are in an open-jaws position and automatically disengages when the set of unitary jaws moves from an open-jaws position to a closed-jaws position.

2. A tool according to claim 1, wherein the tool is a surgical tool.

3. A tool according to claim 2, wherein the surgical tool is configured for simultaneously clamping and cutting tissue.

4. A tool according to claim 1, wherein the lock is a first lock and a second lock.

5. A tool according to claim 1, wherein the lock comprises a first set of components and a second set of components, and the first set of jaws further comprises the first set of components and the second set of jaws further comprises the second set of components.

6. A tool according to claim 5, wherein:
a. the first set of jaws comprises a first working member hingedly connected to a second working member;
b. the first set of components comprise a first latch, a first notched aperture for receiving and securing a second latch, and a first release pin;
c. the first latch and the first release pin are located on either the first working member or the second working member of the first set of jaws and the first notched aperture is located on the other working member of the first set of jaws;
d. the second set of jaws comprises a first working member hingedly connected to a second working member;
e. the second set of components comprises the second latch, a second notched aperture for receiving and securing the first latch, and a second release pin;
f. the second latch and the second release pin are located on either the first working member or the second working member of the second set of jaws and the second notched aperture is located on the other working member of the second set of jaws;
g. wherein the first set of components and second set of components is further arrange such that when the first set of jaws and the second set of jaws are in an open-jaws position and are aligned to form a set of unitary jaws, the first notched aperture receives and engages the second latch, the second notched aperture receives and engages the first latch, and when the set of unitary jaws moves from an open-jaws position to a closed-jaws position the first release pin applies a biasing force on the second latch causing it to disengage from the first notched receiving aperture and the second release pin applies a biasing force on the first latch causing it to disengage from the second notched receiving aperture.

7. A tool according to claim 5, wherein:
a. the first set of jaws comprises a first working member hingedly connected to a second working member;
b. the first set of components comprises a first latch, a first notched aperture for receiving and securing the first latch, a first notched latch, and a first release pin;
c. the first latch and the first notched latch are located on either the first working member or the second working member of the first set of jaws and the first notched aperture and the first release pin are located on the other working member of the first set of jaws;
d. the second set of jaws comprises a first working member hingedly connected to a second working member;
e. the second set of components comprises a second latch, a second notched aperture for receiving and securing the second latch, a second notched latch, and a second release pin;
f. the second latch and the second notched latch are located on either the first working member or the second working member of the second set of jaws and the second notched aperture and the second release pin are located on the other working member of the second set of jaws;
g. wherein the first set of components and second set of components are further arranged such that when the first set of jaws and the second set of jaws are in an open-jaws position and are aligned to form a set of unitary jaws, the first notched latch and the second notched latch engage, and when the set of unitary jaws moves from an open-jaws position to a closed-jaws position the first release pin applies a biasing force on the second notched latch and the second release pin applies a biasing force to the first notched latch causing the first and second notched latches to disengage from one another, and further wherein the set of unitary jaws moves from an open-jaws to a closed-jaws position, the first latch engages with the first notched aperture locking the first set of jaws in a closed-jaws position and the second latch engages with the second notched aperture locking the second set of jaws in a closed-jaws position.

8. A tool according to claim 4, wherein:
a. the tool has a hinge end and a front end;
b. the first lock is located toward the hinge end;
c. the second lock is located at the front end; and,
d. the tool further comprises a latch that engages when the set of unitary jaws is in the closed-jaws position to maintain each of the first set of jaws and the second set of jaws in the closed-jaws position.

9. A tool according to claim 1, wherein the first set of jaws and the second set of jaws each comprise a chamfered outer edge and a saw-tooth inner edge such that the first set of jaws and the second set of jaws fasten together to form the set of unitary jaws with a unitary cutting blade and outer chamfered edges, wherein the unitary cutting blade is a unitary central saw-toothed blade.

10. A tool according to claim 1 further comprising a fail-safe mechanism for releasing the lock if the lock fails to disengage when the unitary jaws move from an open-jaws position to a closed-jaws position.

11. A tool according to claim 1, further comprising a manual lock mechanism for maintaining the jaws in a closed-jaws position, wherein the first set of jaws comprises a first working member hingedly attached to a second working member, the second set of jaws comprises a first working member hingedly attached to a second working member, the manual lock mechanism comprises a first tang hingedly attached to a front end of either the first working member or second working member of the first set of jaws, and a second tang hingedly connected to a front end of either the first working member or second working member of the second set of jaws, a first catch on a front end of the other member of the first set of jaws for receiving and releasably securing the first tang, and a catch on a front end of the other member of the second set of jaws for receiving and releasably securing the second tang.

12. A tool according to claim 1, wherein the first set of jaws comprises a first working member and a second working member connected by a first hinge and the second set of jaws also comprises a first working member and a second working member connected by a second hinge, wherein the tool further comprises a first ratcheting mechanism for the first hinge and a second ratcheting mechanism for the second hinge, which maintain the first set of jaws and the second set of jaws in a closed-jaws position.

13. A tool according to claim 1, wherein the jaw tool comprises a grip with a V-shaped groove to concentrate force on the central cutting blade when the jaw tool moves from the open-jaws position to the closed-jaws position.

14. A tool according to claim 1, wherein the unitary set of jaws has an upper working surface and a lower working surface and the upper working surface has a concave shape and the lower working surface has a corresponding convex shape such that when the unitary set of jaws is in the closed-jaws position the upper working surface is in contact with the lower working surface.

15. A surgical tool comprising two identical separable halves and a lock, wherein:
   a. each half comprises a jaw and a portion of the lock;
   b. the tool is formed by aligning the halves to form a single unitary jaw; and,
   c. the lock on one half engages with the lock on the other half to fasten the halves together when the halves are aligned in an open-jaws position, and automatically unfastens the halves when the tool moves from an open-jaws to a closed-jaws position.

16. A surgical tool consisting essentially of two identical separable halves and an integral lock, wherein:
   a. each half comprises a jaw and a portion of the lock;
   b. the tool is formed by aligning the halves to form a single unitary jaw; and,
   c. the lock on one half engages with the lock on the other half to fasten the halves together when the halves are aligned in an open-jaws position, and automatically unfastens the halves when the tool moves from an open-jaws to a closed-jaws position.

* * * * *